(12) United States Patent
Haskell et al.

(10) Patent No.: US 7,076,106 B2
(45) Date of Patent: Jul. 11, 2006

(54) VIDEO OBJECTS CODED BY KEYREGIONS

(76) Inventors: Barin Geoffry Haskell, 82 Glenwood Dr., Tinton Falls, NJ (US) 07724; Atul Puri, 3660 Waldo Ave., #1A, Riverdale, NY (US) 10463; Robert Lewis Schmidt, 333 Oak Glen Rd., Howell, NJ (US) 07731

( * ) Notice: Subject to any disclaimer, the term of this patent is extended or adjusted under 35 U.S.C. 154(b) by 0 days.

(21) Appl. No.: 10/141,607

(22) Filed: May 9, 2002

(65) Prior Publication Data

US 2002/0159646 A1 Oct. 31, 2002

Related U.S. Application Data

(63) Continuation of application No. 09/654,076, filed on Sep. 1, 2000, now Pat. No. 6,539,121, which is a continuation of application No. 08/986,118, filed on Dec. 5, 1997.

(60) Provisional application No. 60/038,115, filed on Feb. 20, 1997.

(51) Int. Cl.
*G06K 9/36* (2006.01)

(52) U.S. Cl. ............. 382/239; 382/243; 348/434.1

(58) Field of Classification Search .............. 382/239, 382/243, 282, 173, 234; 348/434.1, 521, 348/522; 358/538, 539, 464
See application file for complete search history.

(56) References Cited

U.S. PATENT DOCUMENTS

| 5,086,346 A | 2/1992 | Fujisawa ............... 358/453 |
|---|---|---|
| 5,136,659 A | 8/1992 | Kaneko et al. ........... 382/16 |
| 5,214,721 A | 5/1993 | Fukuhara et al. ......... 382/56 |
| 5,247,590 A | 9/1993 | Fukuhara et al. ......... 382/56 |
| 5,345,317 A | 9/1994 | Katsuno et al. .......... 358/429 |
| 5,566,002 A | 10/1996 | Shikakura ............... 358/433 |
| 5,781,665 A | 7/1998 | Cullen et al. ............ 382/282 |
| 5,790,695 A | 8/1998 | Suwa .................... 382/239 |
| 5,832,115 A | 11/1998 | Rosenberg .............. 382/242 |
| 5,859,921 A | 1/1999 | Suzuki .................. 382/173 |
| 5,912,991 A | 6/1999 | Jeon et al. ............. 382/242 |
| 5,966,468 A | 10/1999 | Fujimoto ............... 382/239 |

FOREIGN PATENT DOCUMENTS

| CA | 2168641 | 8/2000 |
|---|---|---|
| EP | 746159 A3 | 12/1996 |
| EP | 746159 A2 | 12/1996 |

OTHER PUBLICATIONS

International Organization for Standardisation; Generic Coding of Moving Pictures and Associated Audio Information: Video; Recommendation H. 262; ISO/IEC 13818–2 JTC1/SC29/WG11 N0702 (Revised) Incorporating N702 Delta of Mar. 24 and Further Editorial Corrections May 10, 1994.

International Organization for Standardisation; MPEG–4 Video Verification Model Version 2.1; ISO/IEC JTC1//29/WG11 XXXX, May 3, 1996.

International Organization for Standardisation; Working Draft 4.0 of ISO/IEC 14496–2; ISO/IEC JTC1/SC29/WG11 N1797; MPEG97/Stockholm, Jul. 1997.

Digital Multimedia Standards: Digital Video: An Introduction To MPEG–2; Barry G. Haskell, Atul Puri, and Arun N. Netravali; Ch 17–MPEG–4 and the Future, 1997.

*Primary Examiner*—Yon J. Couso

(57) ABSTRACT

A coding protocol provides for coding video data that has been organized as video objects. The protocol provides a keyregion to permit coding of a region of data within the video object having common attributes. According to the protocol a keyregion is identified by a keyregion header, which includes a resync marker that uniquely identifies the keyregion header, a keyregion position signal indicating an origin and a size of the keyregion; and data of the common attribute. Data following the keyregion is coded according to the common attribute.

21 Claims, 4 Drawing Sheets

VIDEO OBJECTS CODED BY KEYREGIONS

CROSS-REFERENCE TO RELATED APPLICATIONS

This application is a rule 1.53(b) Continuation Application of and claim priority to U.S. patent application Ser. No. 09/654,076, filed Sep. 1, 2000; now U.S. Pat. No. 6,539,121 which is a continuation of U.S. patent application Ser. No. 08/986,118, file Dec. 5, 1997; which claims benefit of No. 60/038,115, filed Feb. 20, 1997 which is herein incorporated by reference.

BACKGROUND OF THE INVENTION

The present invention relates to video coding and, more particularly, to the use of video objects in combination with keyregions to improve coding efficiency and image quality.

The advent of video objects and video object planes (VOPs) in video coding permits significant coding savings by selectively apportioning bits among portions of the frame that require a relatively large amount of bits and other portions that require a relatively small number of bits. VOPs also permit additional functionality such as object manipulation.

As an example, FIG. 1(a) illustrates a frame for coding that includes a head and shoulders of a narrator, a logo suspended within the frame and a background. The logo may be static, having no motion and no animation. In such a case, bit savings may be realized by coding the logo only once. For display, the coded logo could be decoded and displayed continuously from the single coded representation. Similarly, it may be desirable to code the background at a low refresh rate to save bits and yet create an illusion of movement in the reconstructed image. Bit savings realized by coding the logo and background at lower rates may permit coding of the narrator at a higher rate, where the perceptual significance of the image may reside. VOPs are suited to such applications. FIGS. 1(b)–1(d) illustrate the frame of FIG. 1(a) broken into three VOPs. By convention, a background generally is assigned VOP0. The narrator and logo may be assigned VOP1 and VOP2 respectively. Within each VOP, all image data is coded and decoded identically.

Not all data within a VOP merits identical treatment. For example, certain regions of a VOP may require animation, whereas others are relatively static. Consider the example of the narrator. The perceptually significant areas of VOP1 center around the facial features of the figure. The narrator's dress and hair may not require animation to the same extent that the facial features do. Accordingly, there is a need in the art for a coding system that emphasizes certain areas of a VOP over others.

Further, regions of a VOP may possess similar characteristics. For example, some image data within the VOP may exhibit the same motion vector or may be quantized according to the same quantization parameters. Certain regions of a VOP may require a greater resilience against channel errors. Coding efficiencies may be obtained by coding the similar attributes only once for the region. Such efficiencies are lost unless coding systems provide a means for coding common attributes of the region differently from other regions in a VOP that do not share the common attributes.

Finally, it may be preferable to embed functionalities in certain regions of a VOP. For example, images may be superimposed upon regions of a VOP. Consider an example where it is desirable to impose a logo image onto the dress of the narrator in VOP1 and permit a viewer to selectively enable or disable display of the logo. Accordingly, there is a need in the art to associate functionalities with certain regions of a VOP.

SUMMARY OF INVENTION

The present invention alleviates the aforementioned needs in the art to a great extent by providing keyregions for VOPs. Keyregions exhibit one or more of the following properties:

they are optional, they consist of a sequence of macroblocks, they are two-dimensional but do not have to be rectangular, a VOP may be portioned into keyregions, but not every macroblock of a VOP must belong to a keyregion, a macroblock that is not a member of a keyregion may be a member of a background keyregion, keyregions begin and end in the same VOP, a macroblock that belongs to a keyregion belongs to only one keyregion, and macroblocks of a keyregion share at least one common attribute.

The keyregion is defined in the coded video information by a keyregion header that identifies the location and width of the keyregion. Data of the macroblocks in the keyregion is decoded by a decoder and placed sequentially within the keyregion until the decoder receives another keyregion header.

DETAILED DESCRIPTION

The present invention provides keyregions to code areas of VOPs at lower bit rates and with improved image quality. Keyregions are a collection of macroblocks within a VOP that are related according to one or more attributes. For example, the macroblocks within a keyregion may have been quantized according to the same quantization parameter, they may exhibit the same motion vector and/or they may possess the same priority. Typically, however, the macroblocks do not merit coding as a separate VOP as the bit costs associated with VOP coding would result in coding inefficiencies. Based on similarities among the macroblocks, coding efficiencies are obtained by organizing the macroblocks into keyregions and coding common information only once.

Figure 1A:
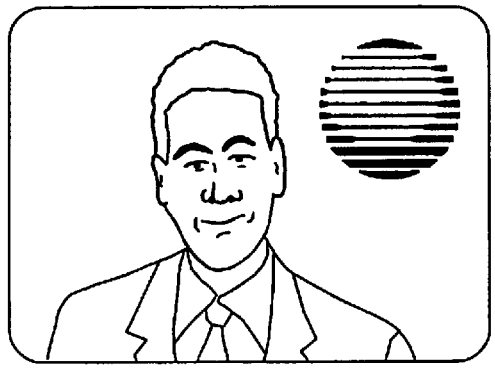
FIG. 1(a) illustrates a video frame to be coded according to the present invention.
Figure 1B:
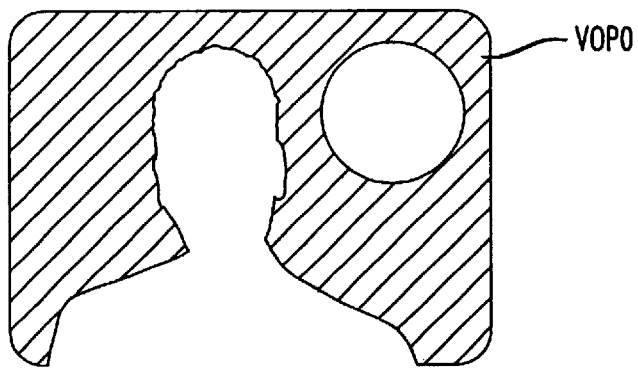
FIGS. 1(b)–1(d) represent video objects from the frame of FIG. 1(a) to be coded according to the present invention.
Figure 1C:
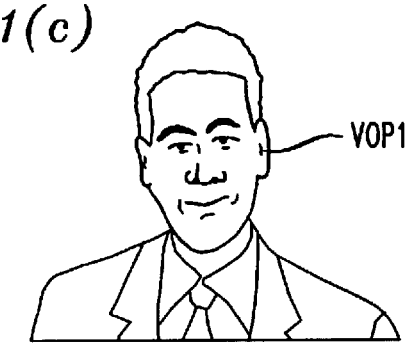
Figure 1D:
Figure 2:
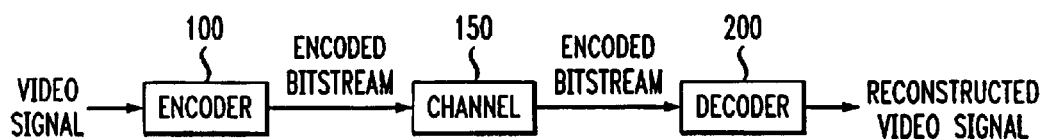
FIG. 2 is a block diagram of the present invention.

According to the present invention, as shown in FIG. 2, an encoder 100 receives a video signal representative of a frame or frames to be coded. The video signal is sampled and organized into macroblocks which are spatial areas of each frame. The encoder 100 codes the macroblocks and outputs an encoded bitstream to a channel 150. The bitstream may identify some macroblocks as having been organized and coded as VOPs. The channel 150 may be a radio channel, a computer network or some storage media such as a memory or a magnetic or optical disk. A decoder 200 retrieves the bitstream from the channel 150 and reconstructs a video signal therefrom for display.

The encoder 100 defines a VOP in the bitstream by generating a VOP header. VOP headers define the position, shape and size of the VOP. As is known, the shape of a VOP may be defined to a pixel or two pixel level. After decoding a VOP header, the decoder 200 knows which macroblocks or portions of macroblocks are members of the VOP and which are not. When implemented with the present invention, the VOP header contains a keyregion enable signal indicating whether the VOP contains one or more keyregions. The keyregion enable signal may be as short as a single bit in a predetermined position of the VOP header.

Figure 3:
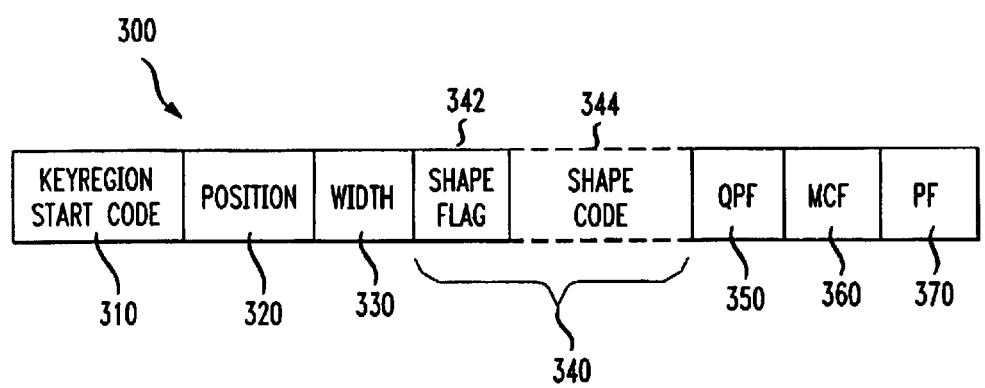
FIG. 3 represents the structure of a keyregion header generated according to the present invention.

In the bitstream, a keyregion is defined by an overhead signal, called a "keyregion header," followed by data for macroblocks of the keyregion. FIG. 3 illustrates the data structure of the keyregion header 300. To indicate the occurrence of a keyregion, the encoder 100 generates a resync marker 310, a code that possesses a unique predetermined bit sequence. The resync marker sequence cannot occur naturally in the VOP. The encoder 100 also generates a macroblock number signal 320 identifying a macroblock that is the origin of the keyregion. For example, the macroblock number 320 may define an address of the upper left hand corner of the keyregion. The macroblock number 320 is a code whose length is determined by the size of the VOP in which the keyregion resides. Also, the encoder 100 generates a keyregion width signal 330 defining the keyregion's width in terms of macroblocks. Again, keyregion width field 330 possesses a length that is determined by the size of the VOP in which the keyregion resides.

The macroblock number and width fields 320 and 330 define a bounding box that circumscribes the keyregion. For example, to code keyregion K1 within VOP1 (shown in FIG. 4), the macroblock number field identifies macroblock MB1 as the keyregion's origin. The width field 330 defines the keyregion to be four macroblocks wide. These fields define a bounding box B1 bounded by lines L1, L2 and L3. The bottom edge of the bounding box B1 is not defined by the macroblock number and width fields. By default, the keyregion is defined to occupy the entire area of the bounding box B1 that falls within the area of VOP1. Thus, the default keyregion includes macroblocks MB3–4, MB6–16, etc. In the VOP header, macroblocks MB1, MB2 and MB5 would have been defined to be excluded from VOP1. If the keyregion takes an irregular shape, as keyregion K1 does in FIG. 4, the shape is defined by a shape refine field 340.

The shape refine field 340 follows the width field 330 in the keyregion header 300. It contains a shape refine flag 342. The shape refine flag 342 is a one bit code that, when enabled, indicates that the keyregion takes an arbitrary shape. If the flag 342 is enabled, it is followed by a shape code 344 that identifies which of the macroblocks contained within a bounding box of the keyregion is found within the keyregion. The shape code 344 provides a bit associated with each macroblock contained in the bounding box provided the macroblock falls within the area of the VOP. The status of the bit determines whether the associated macroblock is included in the keyregion. If the flag 342 is disabled, the shape code 342 is omitted from the shape refine field 340.

Figure 4:
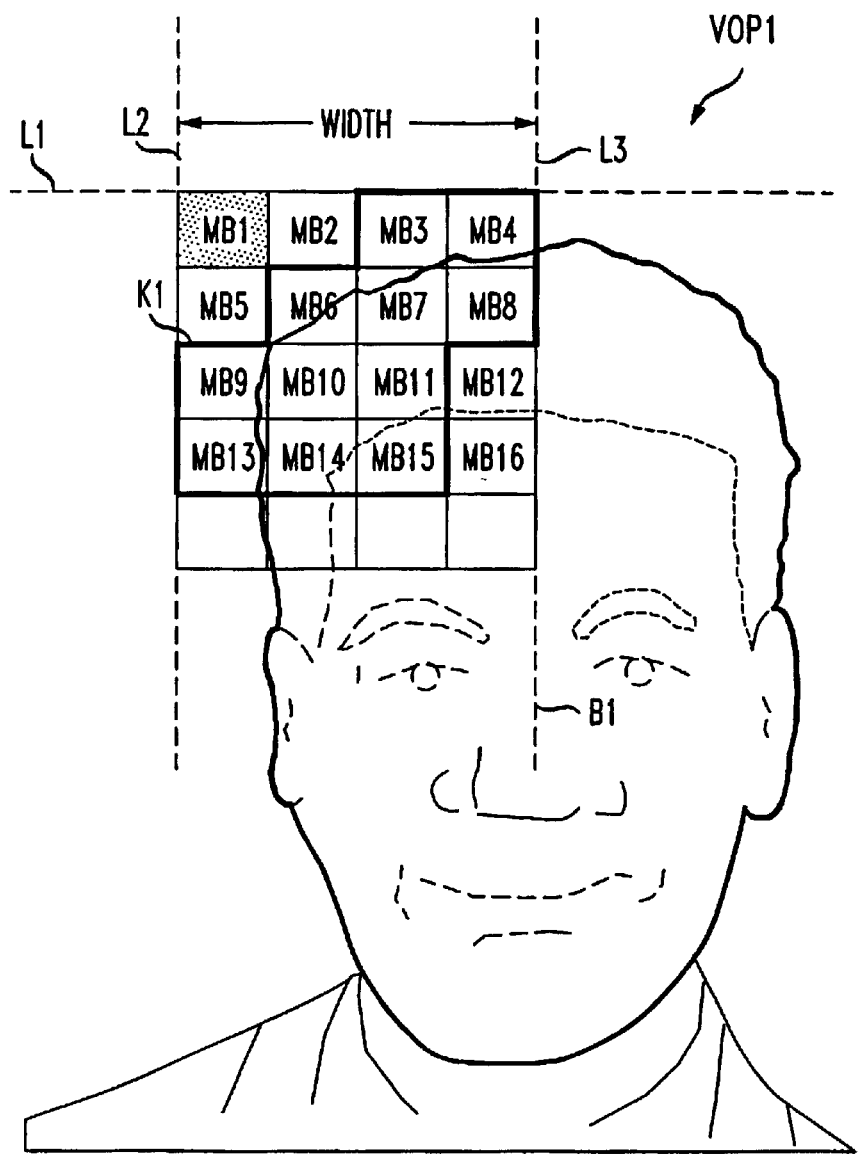
FIG. 4 illustrates a video object coded by keyregion according to the present invention.

Consider again, VOP1 in FIG. 4. As noted, the macroblock number 320 and width 330 fields define the bounding block to every macroblock of VOP1 that falls within a column that begins at macroblock MB1, extends laterally four macroblocks from macroblock MB1 and extends vertically to the bottom of VOP1. However, keyregion K1 is irregular. It includes only macroblocks MB3, MB4, MB6–11 and MB13–15. To define the irregular shape of the keyregion, the shape code 342 will be a thirteen bit code that identifies which macroblocks are part of the irregular keyregion. The following table demonstrates how the shape code 344 defines the membership of each macroblock in keyregion K1:

| Macroblocks of Bounding Box B1 | | | | | | | | | | | | |
|---|---|---|---|---|---|---|---|---|---|---|---|---|
| MB3 | MB4 | MB6 | MB7 | MB8 | MB9 | MB10 | MB11 | MB12 | MB13 | MB14 | MB15 | MB16 |
| Bits in Shape Code | | | | | | | | | | | | |
| 1 | 1 | 1 | 1 | 1 | 1 | 1 | 1 | 0 | 1 | 1 | 1 | 0 |

Again, data for macroblocks MB1, MB2 and MB5 is not provided in the shape code 344 because were defined as not being members of VOP1.

If a shape code 344 is included in the keyregion header 300, the shape code 344 identifies how many macroblocks are contained in the keyregion.

The keyregion header 300 also identifies data that is common throughout the keyregion. For example, a quantization parameter field 350, a motion compensation field 360 and a priority field 370 may be provided for any keyregion. Preferably, each may be identified in the keyregion header 300 by a one bit flag that, if enabled, is followed by a code representing the attribute value. The keyregion may possess more than one common attribute. The decoder 200 uses the common attribute information to decode the macroblocks that follow the keyregion header 300. The keyregion header 300 is followed by a variable length sequence of macroblock data (not shown) representing image data of the macroblocks within the keyregion. For keyregion macroblocks that overlap the edge of the VOP, the decoder interprets encoded data to represent only the portion of the macroblock that falls within the VOP according to conventional encoding.

At the time of this writing, the MPEG-4 video standard is being drafted. The keyregion coding scheme of the present invention has been proposed for integration into the MPEG-4 video standard. Under such proposal, the resync marker 310 is defined as bit sequence of sixteen zeros and a one ("0000 0000 0000 0000 1"). The macroblock number 320 code is a 1–12 bit code representing an address of the top left corner of the bounding box. The code length is determined by the following formula:

$$\text{Length} = \frac{VOP \text{ width}}{16} \times \frac{VOP \text{ height}}{16}.$$

The width field 330 is a 1–7 bit code representing the width of the keyregion in macroblock units. Again, the length of the width field depends upon the width of the VOP. The shape refine field 340 is a one bit code. The quantization parameter value, the priority value and the motion vector values are each two bit codes.

Figure 5:
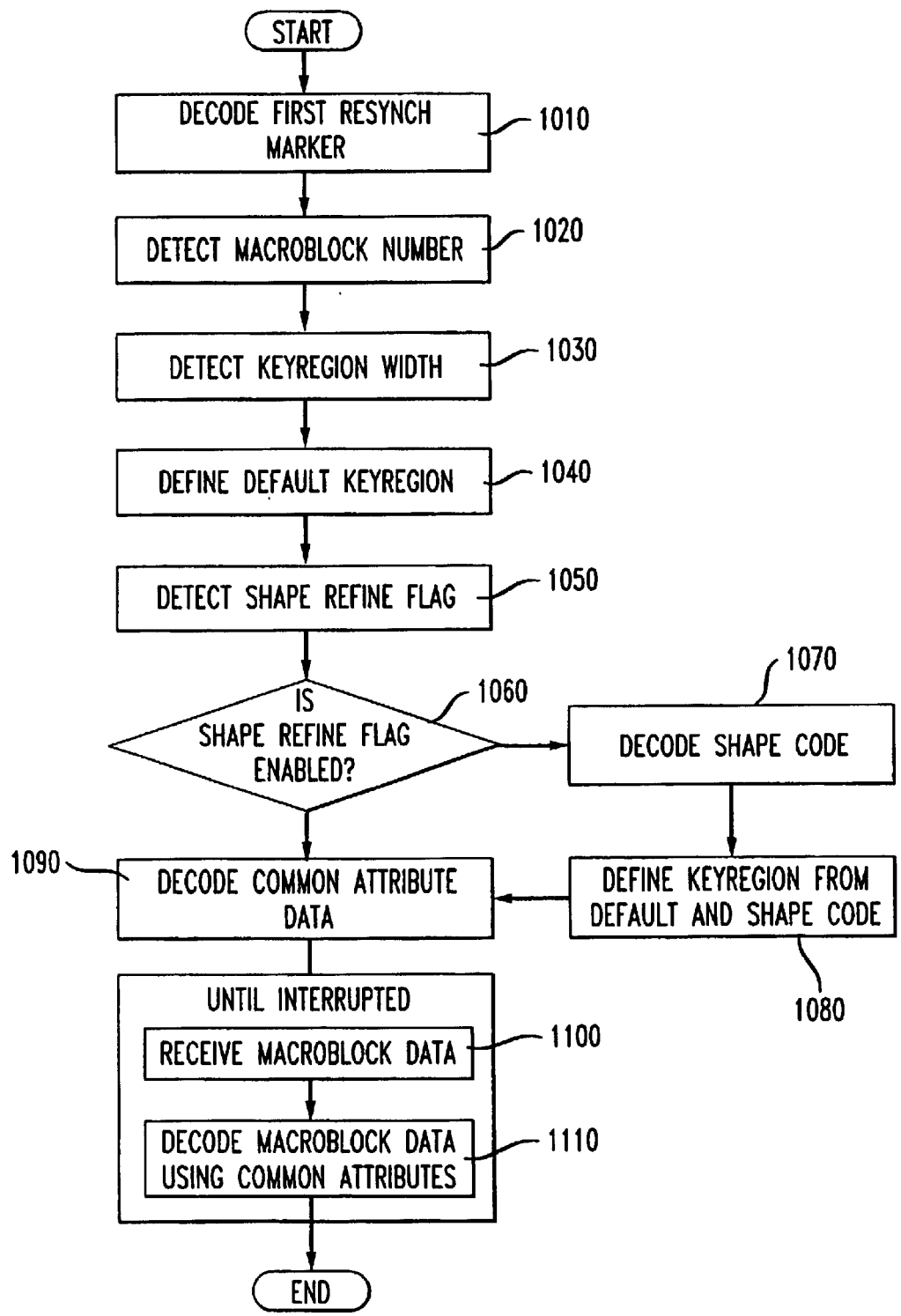
FIG. 5 illustrates the operation of a decoder operating in accordance with the present invention.

FIG. 5 illustrates a method of operation of the decoder 200. The decoder 200 detects the keyregion when it detects the resync marker (Step 1010). The decoder 200 decodes the keyregion header 300 to construct the keyregion. The decoder detects the macroblock number 320 and width 330 fields define the bounding box B1 circumscribing the keyregion K1 (Steps 1020 and 1030). By default, the decoder 200 defines the keyregion to include every macroblock that falls within the union of the VOP and the bounding box B1 (Step 1040). However, the decoder 200 receives the shape refine field (Step 1050). If the shape refine flag 342 is enabled (Step 1060), the decoder 200 decodes the shape code data 344 (Step 1070) to identify macroblocks from the bounding box B1 that are excluded from the keyregion (Step 1080).

The decoder 200 receives and decodes the common attribute data (Step 1090). Using the attribute data, the decoder 200 receives and decodes macroblock data and places each macroblock sequentially in position according to a raster scan direction (left to right, then down) over the keyregion (Steps 1100 and 1110). The decoder 200 does not place decoded data in any position that is not included within the keyregion.

After receiving and decoding the keyregion header 300, the decoder 200 receives all successive data as macroblock data until it is interrupted. For example, following the macroblock data of the keyregion, the bitstream may include another resync marker indicating the beginning of another keyregion. Alternatively, the bitstream may include a succeeding VOP header or another data pattern indicating the occurrence of another type of data. When the decoder 200 detects such a data pattern in the bitstream, it ceases to decode data as macroblock data associated with the keyregion.

The present invention provides a system for encoding and decoding keyregions in video object planes. The keyregions realizes efficient coding of VOP data when a portion of the data share common attributes that are not distributed throughout the entire VOP. For example, when a specific region of a VOP requires coding at a higher resolution than the remainder of the VOP, a single quantization parameter may be set for the region using the keyregion of the present invention. Coding of the high resolution image segment occurs using a greater number of bits than the remainder of the VOP. In this way, bits are conserved in coding the VOP remainder. Also, motion information or priority information may be coded for a keyregion, yielding coding efficiencies that would not be realized if the attribute data were either distributed to the entire VOP or established on a macroblock by macroblock basis.

We claim:

1. A method of encoding video information, comprising:
   receiving data corresponding to a video object plane;
   identifying within the video object plane data a plurality of macroblocks that share a common attribute;
   encoding the identified macroblocks as a keyregion; and
   encoding the remaining macroblocks separately.

2. The method of claim 1, wherein the identified macroblocks and the remaining macroblocks are encoded at different bit rates.

3. The method of claim 1, wherein the common attribute is a quantization parameter.

4. The method of claim 1, wherein the common attribute is a motion vector.

5. The method of claim 1, wherein the common attribute is a display priority.

6. The method of claim 1, further comprising encoding the common attribute only once within the keyregion.

7. The method of claim 1, wherein the keyregion includes a keyregion header and a keyregion body.

8. The method of claim 7, wherein the keyregion header comprises:
   a marker uniquely identifying the keyregion header, and
   a keyregion position signal indicating an origin and a size of the keyregion.

9. The method of claim 8, wherein the keyregion header further comprises a shape refine signal representing a shape of the keyregion.

10. The method of claim 8, wherein the keyregion position signal defines a default keyregion.

11. The method of claim 7, wherein the keyregion body comprises data for the identified macroblocks of the keyregion.

12. A bitstream representing video information, produced by the process of:
    identifying within a received video object plane a plurality of macroblocks that share a common attribute;
    encoding the identified macroblocks as a keyregion within the video object plane, said keyregion including a keyregion header and a keyregion body; and
    encoding the remaining macroblocks separately within the video object plane.

13. The bitstream of claim 12, wherein said keyregion header comprises:
    a keyregion start code identifying the keyregion header, and
    a keyregion position signal indicating an origin and a size of the keyregion.

14. The bitstream of claim 12, wherein said keyregion body comprises data for the identified macroblocks of the keyregion.

15. A machine-readable medium having stored thereon a video file generated according to the process of:
    identifying within a received video object plane a plurality of macroblocks that share a common attribute;
    encoding the identified macroblocks as a keyregion within the video object plane; and
    encoding the remaining macroblocks separately within the video object plane.

16. A machine-readable medium having stored thereon executable instructions that when executed by a processor, cause the processor to encode video information by:
    identifying within a received video object plane a plurality of macroblocks that share a common attribute;
    encoding the identified macroblocks as a keyregion within the video object plane; and
    encoding the remaining macroblocks separately within the video object plane.

17. A method of encoding video information, comprising:
    partitioning video frame data into macroblocks;
    coding selected macroblocks into a video object plane;
    identifying within the video object plane data a plurality of macroblocks that share a common attribute;
    encoding the identified macroblocks as a keyregion within which the shared common attribute is encoded only once; and
    encoding the remaining macroblocks separately.

18. The method of claim 17, wherein the identified macroblocks and the remaining macroblocks are encoded at different bit rates.

19. The method of claim 17, wherein the keyregion includes a keyregion header and a keyregion body.

20. The method of claim 19, wherein the keyregion header comprises:
    a marker uniquely identifying the keyregion header, and
    a keyregion position signal indicating an origin and a size of the keyregion.

21. A method of encoding video information, comprising:
    from a sequence of video data, identifying one or more video objects;
    coding each of a plurality of temporal instances of the video objects as respective video object planes, wherein the coding comprises:
    (1) coding a portion of each of the video object planes as a keyregion, the keyregion being coded with reference to a common attribute, and
    (2) thereafter coding the remainder of each of the video object planes independently from the keyregion.

* * * * *

UNITED STATES PATENT AND TRADEMARK OFFICE
CERTIFICATE OF CORRECTION

| | | |
|---|---|---|
| PATENT NO. | : 7,076,106 B2 | Page 1 of 1 |
| APPLICATION NO. | : 10/141607 | |
| DATED | : July 11, 2006 | |
| INVENTOR(S) | : Barin Geoffry Haskell et al. | |

It is certified that error appears in the above-identified patent and that said Letters Patent is hereby corrected as shown below:

Title page, Item (60), Related U.S. Application Data, should read:

--Provisional application No. 60/038,015, filed on Feb. 14, 1997.-- to replace

"Provisional application No. 60/038,115, filed on Feb. 20, 1997."

Signed and Sealed this

Second Day of January, 2007

JON W. DUDAS
*Director of the United States Patent and Trademark Office*